United States Patent [19]

Farbood et al.

[11] Patent Number: 6,165,517
[45] Date of Patent: Dec. 26, 2000

[54] PROCESS FOR PREPARING ACETOPHENONE, PRODUCTS PRODUCED THEREFROM AND ORGANOLEPTIC USES OF SAID PRODUCTS

[75] Inventors: Mohamad I. Farbood, State College, Pa.; Augustine Yonghwi Kim, Morganville; Robert W. Blocker, Brick, both of N.J.

[73] Assignee: International Flavors & Fragrances Inc., New York, N.Y.

[21] Appl. No.: 09/336,052

[22] Filed: Jun. 18, 1999

[51] Int. Cl.[7] .............................. A23L 1/23; A23L 2/56; C12P 7/24; C12R 1/01; C12R 1/06
[52] U.S. Cl. .......................... 426/60; 426/534; 426/538; 426/650; 435/147; 435/822; 435/830
[58] Field of Search ...................... 426/534, 650, 426/60, 533, 538; 512/27; 435/280, 147, 830, 822

[56] References Cited

U.S. PATENT DOCUMENTS 4,871,688  10/1989  Hilton et al. .............................. 435/147
5,036,004  7/1991  Majima et al. ........................... 435/116

*Primary Examiner*—Gabrielle Broullette
*Assistant Examiner*—R. Madsen
*Attorney, Agent, or Firm*—Arthur L. Liberman

[57] ABSTRACT

A process for producing acetephenone from a source of cinnamic acid is carried out with high amounts of oxygen and sugar in the presence of a bacteria species. Fragrance compositions and foodstuff compositions are augmented and enhanced by the presence of the product compound.

13 Claims, 7 Drawing Sheets

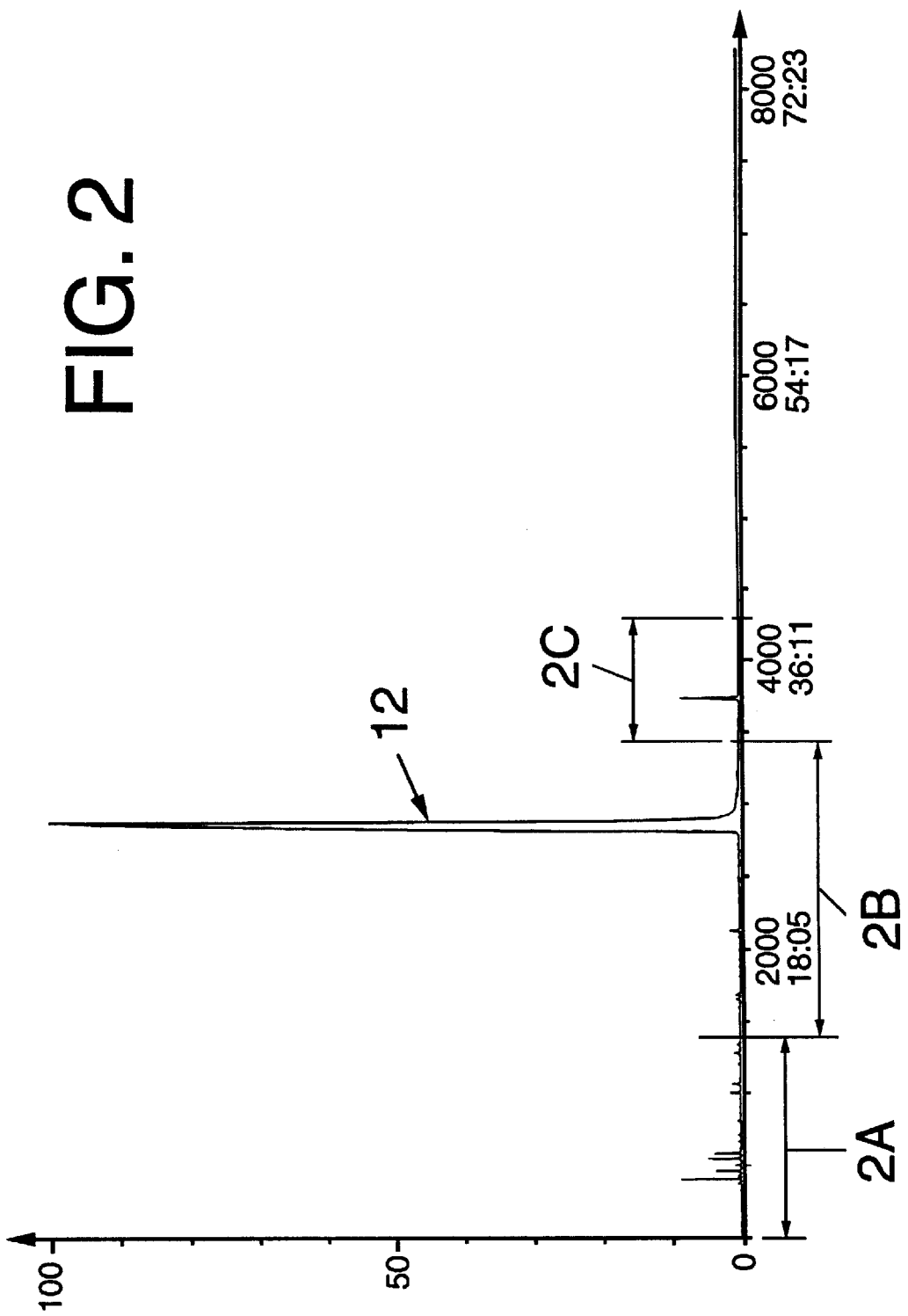

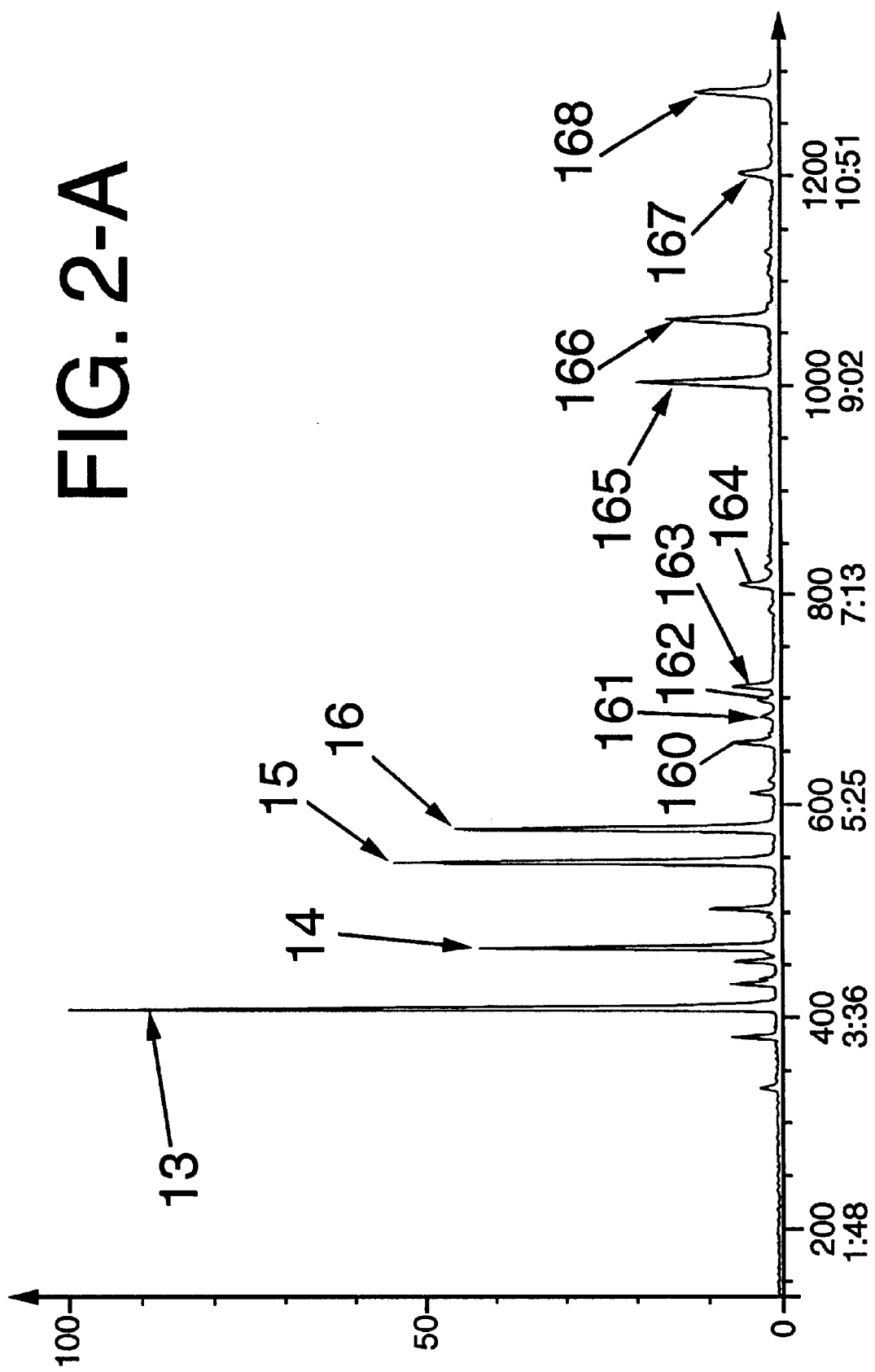
FIG. 2-A

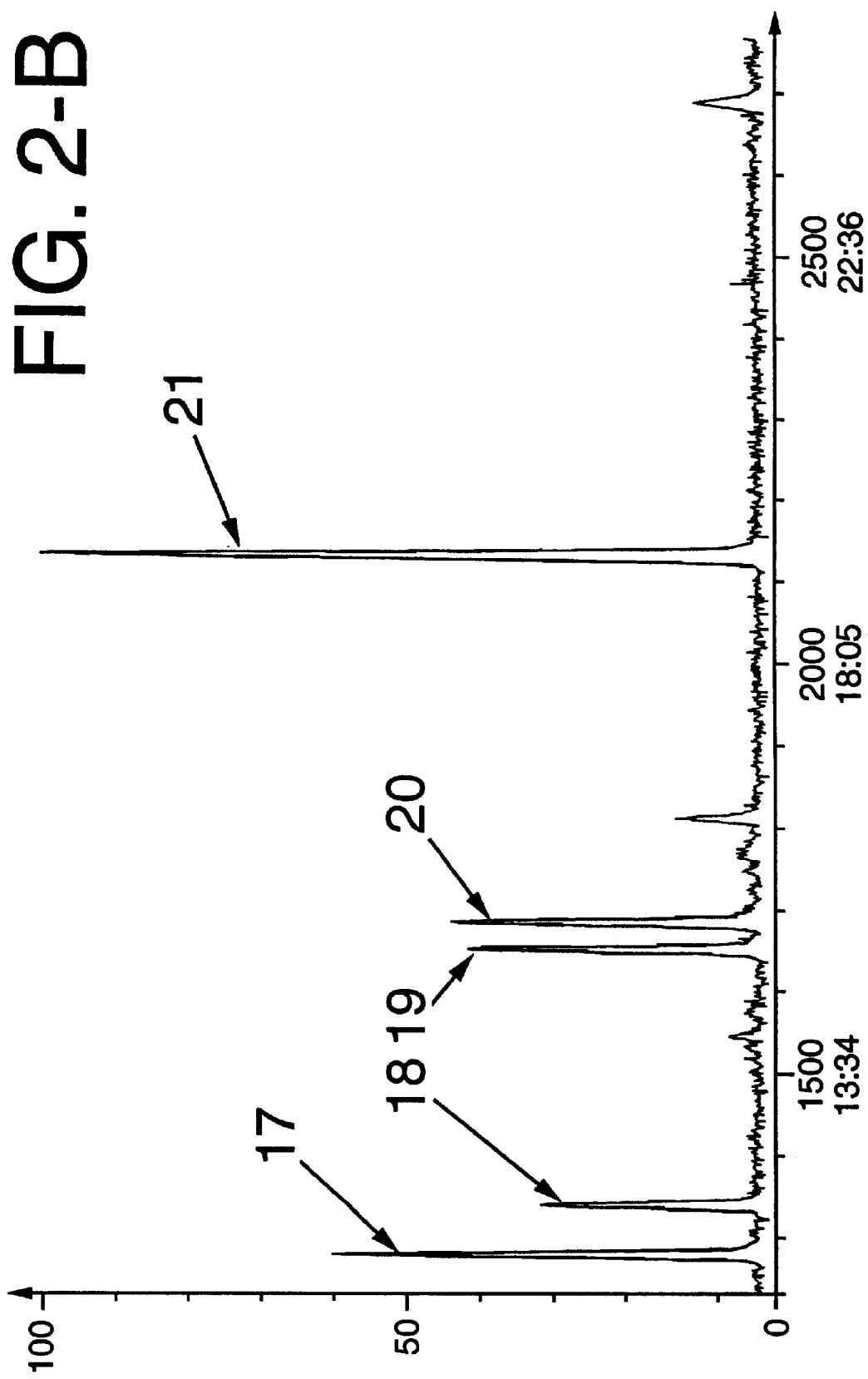

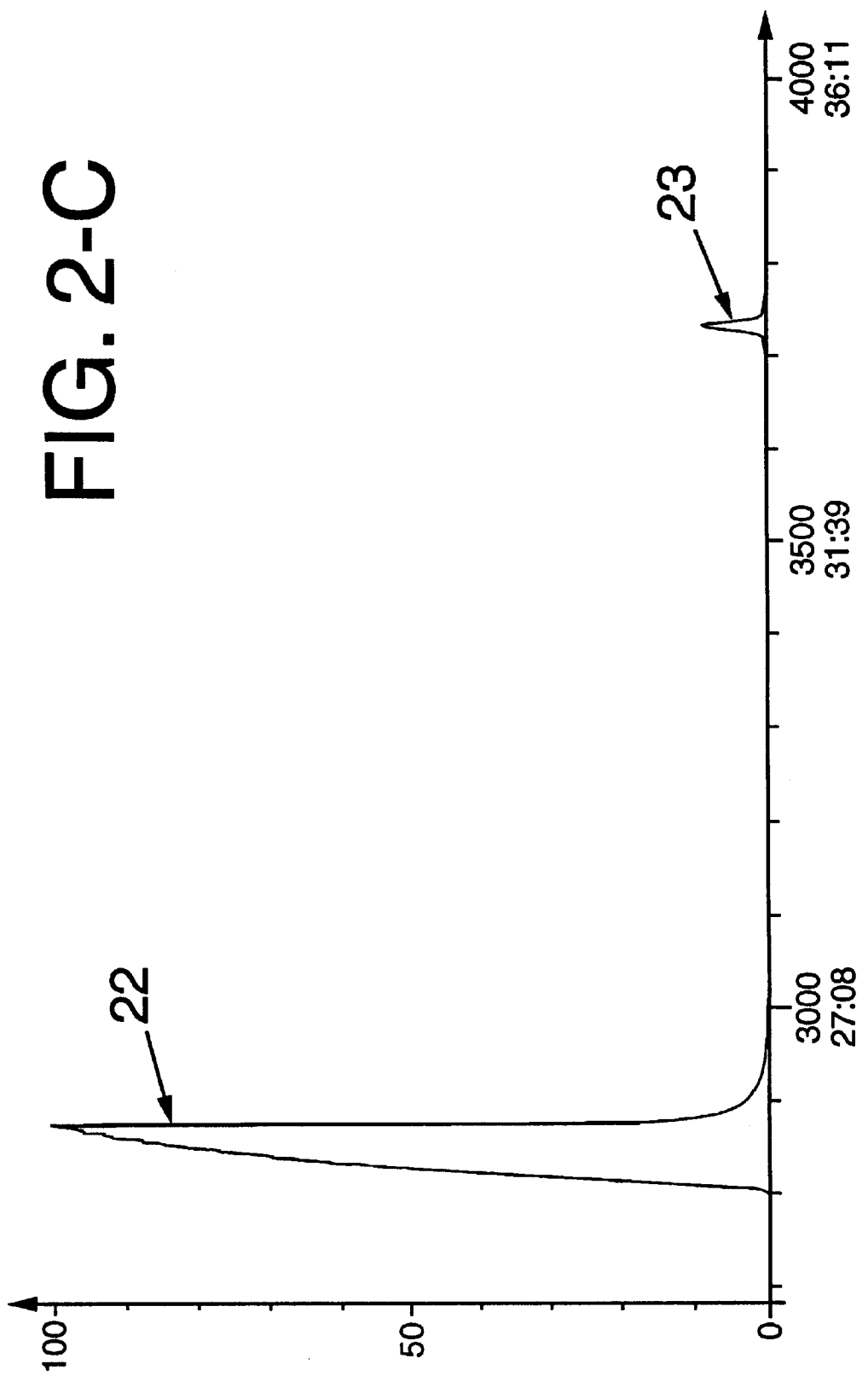
FIG. 2-C

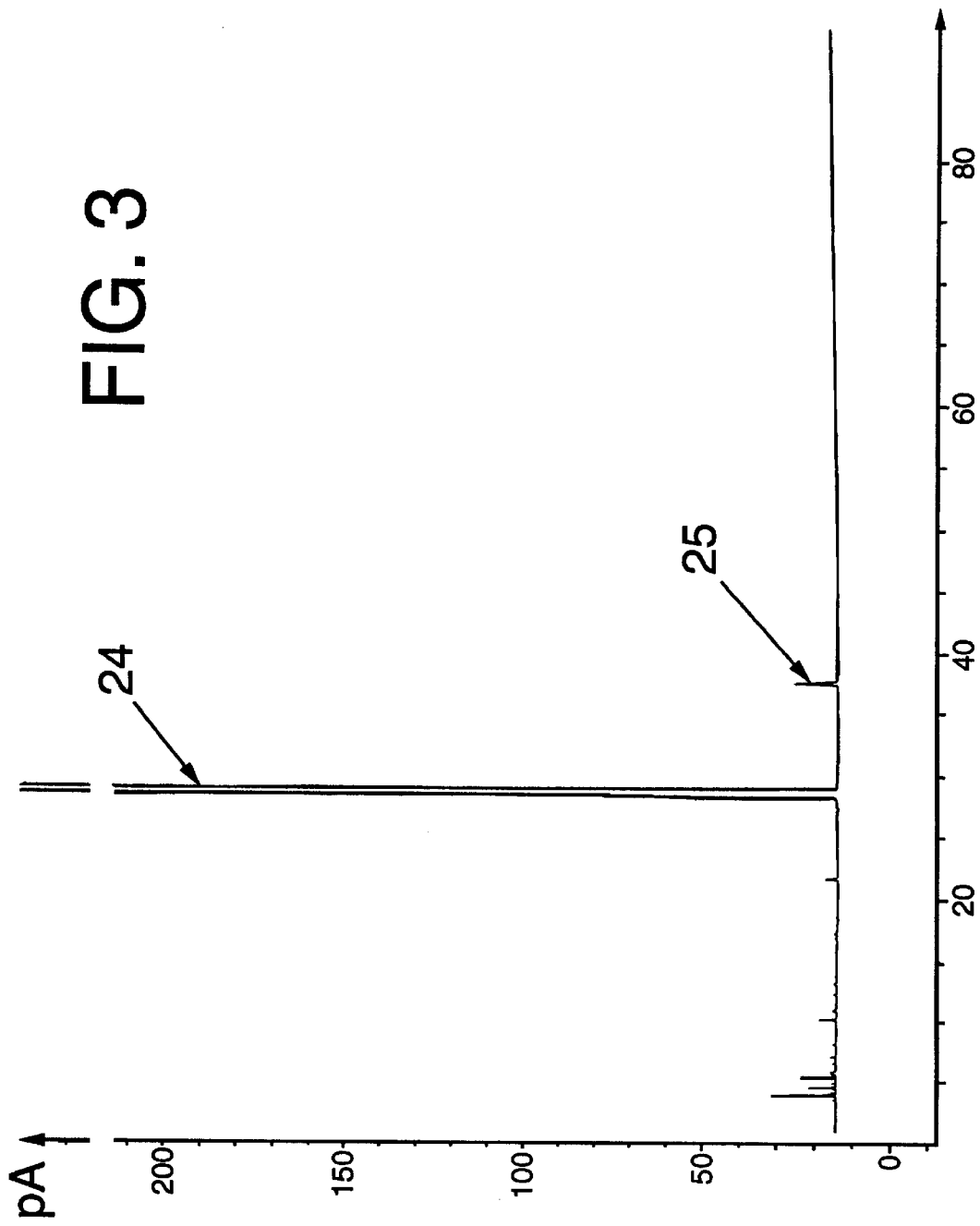

PROCESS FOR PREPARING ACETOPHENONE, PRODUCTS PRODUCED THEREFROM AND ORGANOLEPTIC USES OF SAID PRODUCTS

INTRODUCTION AND BACKGROUND

The present invention relates to a microbial process for the preparation of compositions containing acetophenone. In a further aspect, the present invention relates to products produced by the microbial process.

In a still further aspect, the present invention relates to organoleptic uses of said products.

In today's market, it is frequently desirable to identify flavor components of food items and other consumer products as containing "natural flavors" or "natural ingredients." It is generally recognized in the industry that a flavor compound having been prepared by microbial processes can be designated as a natural product and therefore have an important place in the commercialization of products containing them. As a result, the industry has devoted considerable time and effort to develop methods for the production of ingredients for food and other consumer items and in particular for the production of acetophenone which can be called "natural."

Thus, as an example of such prior developments a method for preparing acetophenone utilizing a mutant microorganism of the microbial genus Pseudomonas is disclosed in U.S. Pat. No. 4,871,668. The nutrient medium contains a cinnamate compound as a carbon source. However, the procedure shown therein utilizes an unknown microorganism with the deposit number ATCC 53716 which process is not shown to be broadly applicable to other types of microbes. In a study by the same inventors in *APPLIED AND ENVIRONMENTAL MICROBIOLOGY* of March 1990, pages 623–627, there is disclosed that an unclassified Pseudomonas species can be used to form acetophenone from cinnamic acid.

A number of studies have shown that acetophenone can be metabolized by certain species of Arthrobacter and Nocardia in *Eur. J. Biochem.*, 86, 175–186 (1978). There are also some studies showing liquidation of acetophenone by certain bacterial species as shown in *Biosci. Biotech. Biochem., Vol.* 59, (12), pages 2324–2325, 1955. Other studies involving bacterial degradation and metabolism of the acetophenone are found in *APPLIED AND ENVIRONMENTAL MICROBIOLOGY, September* 1979, pages 514–520, May 1987, pages 1103–1112 and December 1990, pages 3678–3685. Oxidative production of acetophenone is reported by Ohta, et al. in *Agric. Bio. Chem., Vol.* 48 (6), 1509–1516, 1984.

Conversion of 1-phenethyl alcohol to acetophenone utilizing a microbe is shown by Lee, et al. in *APPLIED AND ENVIRONMENTAL MICROBIOLOGY*, September 1996, pages 3101–3106. Ethylbenzene converted to 1-phenethyl alcohol and acetophenone utilizing fungi is shown by Holland, et al. in *CAN. J. CHEM., Vol.* 65, 1987, page 502 et seq.

Use of Arthrobacter for transforming n-hexadecane to ketones is shown by Klein, et al., *APPLIED MICROBIOLOGY,* May 1969, pages 676–681.

Production of ketones and alcohol using Arthrobacter with metabolism of cyclohexaneacetic acid is described by Ougham, et al. in the *JOURNAL OF BACTERIOLOGY,* June 1982, pages 1172–1182.

Metabolism of acetophenone is shown by Cripps in the *Biochem J. (Great Britain),* 1975, Vol. 152, pages 233–241.

The Arthrobacter genus of bacteria is well known and described in the literature.

Such prior art methods are said to be economically attractive but there is a constant need for improvement of yields and conversion which is addressed in this invention.

In the flavor and fragrance art, the need has arisen for the development of more efficient production of acetophenone which has heretofore been found to be useful and necessary in the creation of flavor formulations used in augmenting or enhancing the aroma or taste of such items as foodstuffs, chewing gums and toothpastes, and which is also useful in augmenting or enhancing the aroma of perfume compositions such as colognes, perfumed articles in either solid or liquid state as, for example, ionic, cationic, nonionic or zwitterionic detergents, perfumed polymers, fabric softener compositions, fabric softener articles, hair preparations, cosmetic powders and the like.

It is therefore an object of the present invention to provide a new and improved method for preparing acetophenone by a fermentative process to result in a natural ingredient suitable for a wide variety of purposes.

It is a further object of the present invention to produce acetophenone in a more efficient manner to obtain a higher yield and greater conversion than prior known biological methods.

SUMMARY OF THE INVENTION

The above and other objects and features of the invention are obtained in accordance in the present invention by carrying out a fermentation process using selective reaction techniques to produce and recover acetophenone which is useful for its organoleptic properties in augmenting or enhancing the aroma or taste of consumable materials such as foodstuffs, chewing gums, toothpastes, perfume compositions, colognes and perfumed articles such as solid or liquid detergents, perfumed polymers, fabric softener compositions, fabric softener articles, cosmetic powders, hair preparations and the like.

Acetophenone is represented by structure:

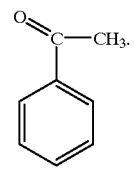

The fermentation reaction to produce acetophenone according to the invention is carried out under oxidative conditions by preparing an aqueous inoculum nutrient medium including a selected bacterium species in a first liquid phase, and a second liquid phase containing a source of cinnamic acid, either as the free acid or a salt thereof in the form of a cinnamate. Cinnamic acid is represented by the structural formula:

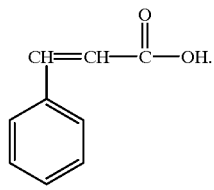

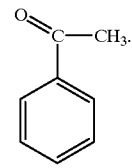

Alkali metal salts such as sodium cinnamate have also been found to yield good results for this fermentation reaction.

The inoculum medium containing the usual buffers, mineral salts, yeast extract and the like is an aqueous, generally neutral pH system and is sterilized. Then the aqueous material medium is inoculated with the selected bacterium species and incubated for a sufficient period of time with sufficient vigorous agitation to form a viable culture.

The second phase is the acetophenone production system containing essentially the same components as the inoculum medium. This is also sterilized.

The first liquid phase and the second liquid phase are then mixed together with agitation to form a single-phase system and permitted to undergo further incubation. Then the source of cinnamic acid is added in increments at a rate sufficient to maintain a concentration of cinnamic acid equivalent to at least 5 g/l[e.g. 5–10 g/l]. The broth is initially neutral at approximately pH=7. At the conclusion of the fermentation, the broth is acidified to pH 4. Following recovery, the product is obtained in a yield of at least 90% to 99+%.

A further feature of the present invention resides in the products produced by the present invention characterized by the GLC profiles which accompany this application.

Still further, another feature of the invention resides in the flavor and fragrance compositions containing the acetophenone produced by the present invention.

BRIEF DESCRIPTION OF THE DRAWINGS

The present invention will be further understood with reference to the accompanying drawings wherein.

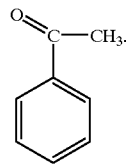

FIG. 2 is a mass spectrum for the reaction product of Example 2 containing the acetophenone compound having the structure:

FIG. 2A is an enlarged section of that portion of the mass spectrum of FIG. 2 indicated by the identifier "A" for the reaction product of Example 2 and containing peaks for a number of different compounds.

FIG. 2B is an enlarged section of that portion of the mass spectrum of FIG. 2 indicated by the identifier "B" for the reaction product of Example 2 and containing peaks for a number of different compounds including as the major peak benzaldehyde having the structure:

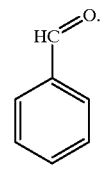

FIG. 2C is an enlarged section of the mass spectrum of FIG. 2 indicated by the identifier "C" for the reaction product of Example 2 and containing the peak for acetophenone having the structure:

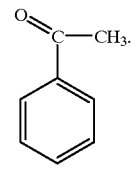

FIG. 3 is a mass spectrum for the reaction product of Example 3 containing the acetophenone compound having the structure:

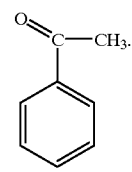

Figure 4:
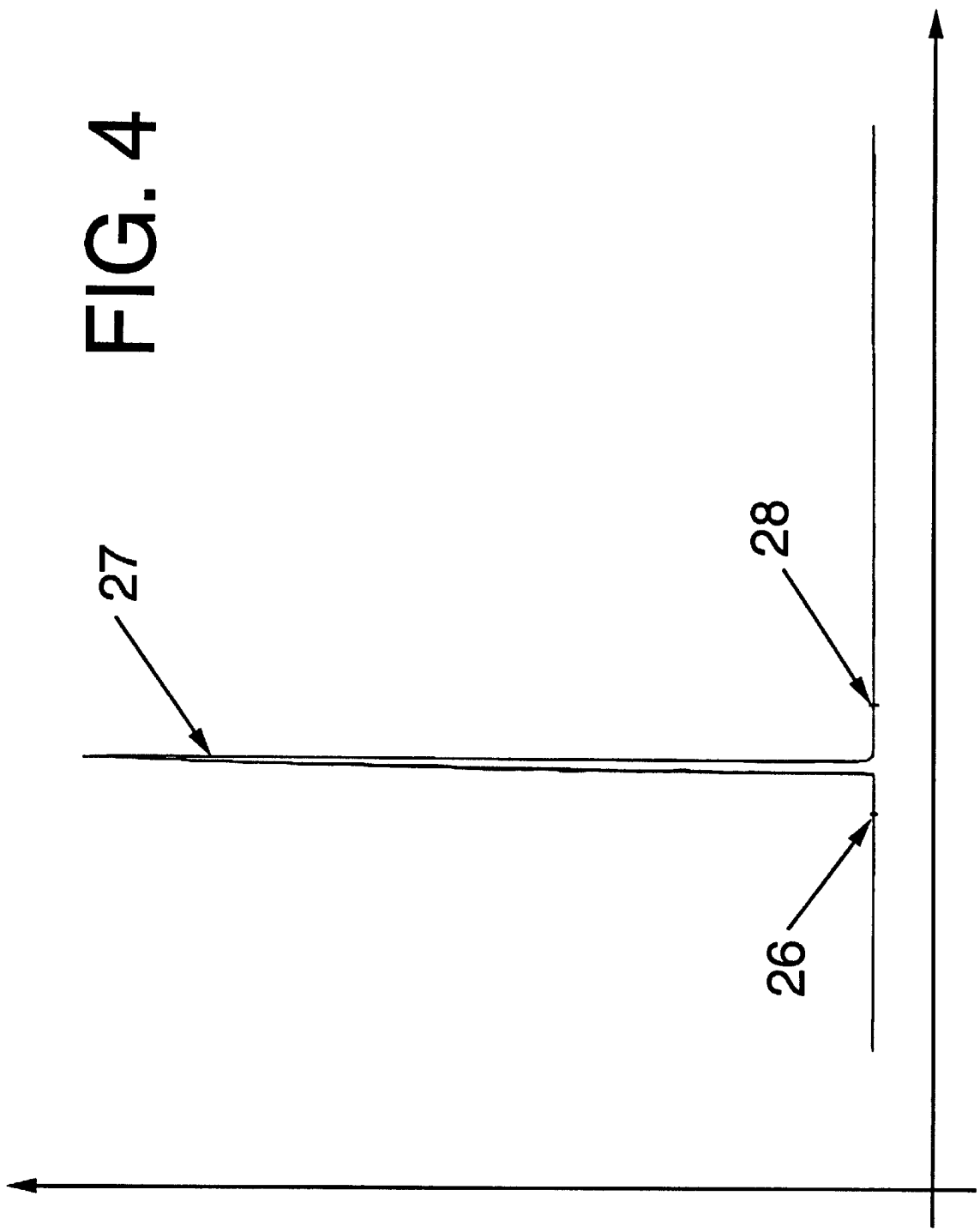

FIG. 4 is a GLC profile for the reaction product of Example 4 containing the acetophenone compound having the structure.

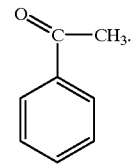

DETAILED DESCRIPTION OF INVENTION

The reaction according to the present invention is shown thusly:

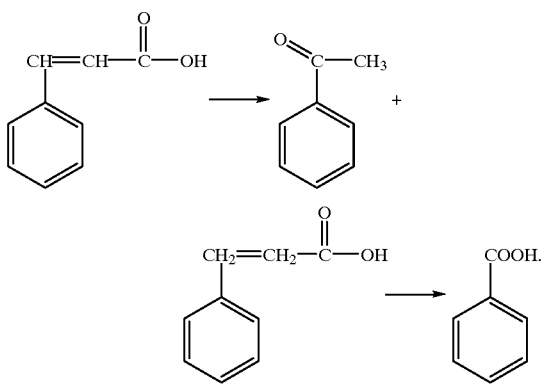

More specifically, the oxidative reaction involves the use of an oxygen containing gas such as air or oxygen which is dissolved in a controlled amount into the reaction medium sufficient to maintain oxidative conditions for the reaction. In the process of the invention the microbe species that is preferably used are *Comamonas testosteroni* and Arthrobacter.

The process is carried out by first preparing an inoculum medium containing a yeast extract, buffers, one or more mineral salts and water to form a suitable medium to serve as a host for the bacteria. Typically the inoculum medium is sterilized for a sufficient period of time.

Thereafter the selected bacteria species is used to inoculate the medium and a carbon source is introduced therein with agitation and the temperature is maintained at least at about 20–30° C. The medium is then maintained under these conditions to grow the bacteria into a grown culture which typically requires about 20 to 30 hours. A reaction vessel is also prepared to contain a production medium, typically including a buffering agents such as $KH_2PO_4$, a yeast extract and other nutrient sources which may include trace minerals and growth factors. Generally neutral conditions prevail.

Typically sources of carbon include sugars such as glucose and dextrose, as well as carboxylic acids such as succinic acid, butyric acid and the like. Alkali metal salts and alkaline earth metal salts can be used.

Following preparation of the acetophenone production medium, the medium is sterilized for a sufficient period of time. After that, the inoculum medium is introduced into the reaction vessel containing the acetophenone production medium, which can be the same or different.

Following inoculation with the bacteria species, and with commencement of feeding of the nutrient medium, a source of cinnamiz acid, such as an alkali metal salt of cinnamic acid; e.g. sodium cinnamate, is pumped into the reaction vessel.

The nutrient feed which contains the carbon source and may also contain a solution of vitamins as desired and trace mineral solutions as desired as well as buffers, and the like is pumped into the reaction vessel.

It is to be understood that the production medium and the nutrient medium suitable for the present invention are well known and understood by persons skilled in the art.

The oxidative reaction is permitted to proceed being careful to maintain oxidative conditions in the reaction vessel by balancing carbon source feed and oxygen injection into the system. The concentration of the carbon source is maintained at least about 0.01 grams per liter to as much as 1.5 grams per liter, preferably 0.1 to 0.5 grams per liter, most preferably at about 0.03–0.07 grams per liter during the fermentation reaction. The actual concentrations varies at any given time from a minimum to a maximum recognizing that too high a carbon concentration will result in production of undesired products instead of the desired product. By automatic addition of the nutrient feed, the nutrient feed rate can range from about 5 to about 72 grams per liter per hour.

The desired temperature of the reaction is approximately 30° C. although this can vary as will be understood by persons skilled in this art. The optimum temperature of the reaction can be readily determined by skilled operators using parameters well understood in the fermentation art. A typical range of temperature is 20 to 50° C. It is a feature of the oxidation fermentation reaction of the present invention to avoid the formation of excessive amounts of undesired products which are typically produced in prior known methods. Under the reaction conditions discovered by applicants, unwanted product production is avoided by a inventive control of the carbon source addition, the addition of the source of cinnamic acid and charging of the oxygen source to the system. Thus, the rate of carbon source addition and oxygen source addition is such as to maintain oxidation conditions in the reaction medium and enabling the cinnamate compound to be converted to the desired product and thereby control the reaction to form acetophenone product and avoid the formation of excessive unwanted products.

As an example of oxygen in the system, the oxygen is introduced at a rate which is at least about 0.1 liters per liter of reaction mixture. The injection of air or other oxygen containing gas is controlled so as to measure at least 10% dissolved oxygen as measured by a standard oxygen probe at all times during the reaction. Typical dissolved oxygen readings during the reaction are 68% to 98%.

The resulting acetophenone is useful in augmenting or enhancing the aroma or taste of consumable materials as set forth herein.

The form in which the microorganism bacteria strain is used is not critical. It can be used as a culture in a suspension including the cells and the corresponding nutrient solution or in the form of cells suspended in a buffering solution. The cells or an enzyme extract thereof may be immobilized on a suitable solid support which may then be used to effect the transformation.

The bacteria species that have been found suitable for practice of this invention are:

Arthrobacter sp. ATCC 25581;

*Comamonas testosteroni* ATCC 11996;

*Comamonas testosteroni* ATCC 17409;

*Comamonas testosteroni* ATCC 15666; and

*Comamonas testosteroni* ATCC 17409.

The culture suspension is prepared by inoculation of a suitable medium with the microorganism. A suitable medium is one which contains carbon sources, nitrogen sources, inorganic salts and growth factors. Among the suitable carbon sources are for example, glucose, galactose, L-sorbose, maltose, sucrose, cellobiose, trehalose, L-arabinose, L-rhamnose, ethanol, glycerol, L-erythritol, D-mannitol, lactose, melibiose, raffinose, melezitose, starch, D-xylose, D-sorbitol, alpha-methyl-D-glucoside, lactic acid, citric acid, butyric acid and succinic acid. Among the suitable nitrogen sources are, for example, nitrogen containing organic substances such as peptone, meat extract, yeast extract, corn steep liquor, casein, urea, amino acids, or nitrogen containing inorganic compounds such as nitrates, nitrites, and inorganic ammonium salts. Among the suitable inorganic mineral salts are, for example, phosphates of magnesium, potassium, calcium, and sodium. The above-mentioned nutrients in the culture medium may be supplemented with, for example, one or more vitamins of the B Group and/or one of more trace minerals such as Fe, Mo, Cu, Mn, B as desired. However, the process can be performed in a vitamin-free medium; for example, when a small amount of yeast extract is added to the medium there is no need for vitamins or trace minerals.

The cultivation of the microorganism can be carried out as a stationary culture or as a submerged culture (e.g. shaking culture, fermentors) preferably under aerobic conditions. One suitably may work in the pH range of from about 3.5 to about 8.0, and preferably in the range of from about 4.0 to about 7.5. The pH may be regulated by the addition of inorganic or organic bases, such as aqueous or gaseous ammonia, sodium hydroxide, potassium hydroxide, calcium hydroxide, calcium carbonate, by ion-exchange resins, or by the addition of a buffer such as phosphate or phthalate. The incubation temperature is suitably maintained at between about 15° C. and about 33° C., with a range from about 20° C. to about 30° C. being preferred.

The process in accordance with the invention is conveniently carried out by adding a source of sugar, such as dextrose or glucose to the culture medium at the onset of cultivation, as the carbon source. Alternatively, the dextrose or glucose may be added in combination with another carbon source, as mentioned above, either during cultivation, or when the cultivation is complete. The amount level, or concentration of the substrate in the medium may vary. For example, in the case of sources of sugar, levels of from about 0.3% to about 5% may make up the medium initially or be added during the course of the oxidative growth, although the specific level of carbon source may be easily determined and can be varied.

The reaction time may vary depending on the composition of the culture medium and the substrate concentration. In general, shaking flask cultures require from between about 2 h. and about 240 h. depending upon the microorganism and the composition of the culture medium. However, when a fermenter vessel is used the oxidative reduction reaction time may be reduced to about 100 h. or less.

The reaction of this invention may be carried out using the bacteria isolated from the culture solution. In this case, the reaction can be conveniently carried out in aqueous solution, for example, in a buffer solution, in a physiological salt solution, in a fresh nutrient solution, or in water. The isolated cells may be immobilized on a solid support and the desired transformation effected in the absence of the live microorganism. The transformation of the substrate may be effected by mutants of the microorganism. Such mutants can be obtained readily by methods well known in the art.

Conventional antifoam agents, such as silicone oils (e.g., UCON®), polyalkyleneglycol derivatives, maize oil, or soya oil can be used to control foaming as is known in the art.

The acetophenone obtained in accordance with the present invention and one or more auxiliary perfume ingredients, including for example, hydrocarbons, alcohols, ketones, aldehydes, nitrites, esters, ethers, synthetic essential oils, lactones other than those of our invention, and natural essential oils may be admixed so that the combined odors of the individual components produce a pleasant and desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual compositions which contribute to their particular olfactory characteristics, however, the overall sensory effect of the perfume composition will be at least the sum total of the effects of each of the ingredients. Thus, the acetophenone of this invention can be used to alter, modify or enhance the aroma characteristics of a perfume composition, for example, by utilizing or moderating the olfactory reaction contributed by another ingredient in the composition.

The amount of the acetophenone of this invention which will be effective in perfume compositions as well as in perfumed articles and colognes depends upon many factors including the other ingredients, their amounts and the effects which are desired. It has been found that perfume compositions containing as little as 0.005% of acetophenone or even less (e.g., 0.0025) can be used to impart a variety of aromas and tastes. For example, it can have a cherry, benzaldehyde-like, mimosa-like, cinnamic aroma with sweet brown-bready caramel notes and taste, with sweet creamy, dairy, earthy, chocolate undertones and a graining nuance.

It may also be described as providing a bitter nutty aroma with a chocolate topnote, a balsamic-resinous aroma and taste with cooked undertones; a floral-honey-almond aroma with clean and fresh nuances; a heavy anis-waxy aroma and taste with fresh nuances or a fresh-fruity aroma and taste with a sweet almond-hazelnut note. Such aromas can be imparted to soaps, cosmetics, detergents including anionic, cationic, nonionic and zwitterionic solid or liquid detergents, perfumed polymers and other products as desired. The amount employed can range up to 70% of the fragrance components and will depend upon the consideration of cost, nature of the end product, the effect desired on the finished product and the particular fragrance sought.

The acetophenone of this invention are useful when either taken alone or take together with other perfumery ingredients in detergents, soaps, space odorants and deodorants, perfumes, colognes, toilette waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of acetophenone can suffice to impart intense, substantive, sweet, fresh fruity, cherry aroma with sweet, creamy, and nut like topnotes and heavy fruity and cherry undertones to floral and patchouli perfume formulations. Generally no more than 5% of the acetophenone based on the ultimate end product is required to be used in the perfume compositions.

Furthermore, as little as 0.25% of the acetophenone can suffice to impart such aromas to perfumed articles per se, whether in the presence of other perfume materials or whether used by themselves. Thus, the range of use of the acetophenone of this invention in perfumed articles, e.g., perfumed polymers and solid or liquid anionic, cationic, nonionic or zwitterionic solid or liquid detergents, may vary from 0.25% up to about 5% by weight based on the total weight of the perfumed article.

In addition, the perfume composition or fragrance composition of our invention can contain a vehicle or carrier for the acetophenone. The vehicle can be a liquid such as a non-toxic alcohol, e.g., ethanol, a non-toxic glycol, e.g., propylene glycol, or the like. The carrier can also be an absorbent solid such as a gum (e.g, gum arabic or xanthan gum or guar gum) or components for encapsulating the composition by means of coacervation (such as by gelatin) or by means of formulation of a polymer around a liquid center. This can be accomplished by using urea formaldehyde prepolymer to form a polymeric capsule around a perfume composition center as is known in the art.

It will be appreciated from the present disclosure that the acetophenone of the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplement the existing flavor impression to modify its organoleptic character.

The term "enhance" is intended herein to mean the intensification (by use of the saturated lactone compound of this invention) of a flavor or aroma note or nuance in a foodstuff or perfume composition or perfumed article without changing the quality of said note or nuance.

A "flavoring composition" as referred to herein means one which contributes a part of the overall flavor impression by supplementing or fortifying a natural or artificial flavor in a material or one which supplies substantially all the flavor and/or aroma character to a consumable article.

The term "foodstuff" as used herein includes both solid and liquid ingestible material for man or animals which materials usually do, but need not, have nutritional value. Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products, and the like.

When the acetophenone of this invention is used in a flavoring composition, it can be combined with conventional flavoring materials or adjuvants. Such co-ingredients or flavoring adjuvants are well known in the art for such and have been extensively described in the literature. Requirements of such adjuvant materials are: (1) that they be non-reactive with the acetophenone of this invention; (2) that they be organoleptically compatible with acetophenone of this invention whereby the flavor of the ultimate consumable material to which the acetophenone is added is not detrimentally affected by the use of the adjuvant; (3) that they be ingestibly acceptable and thus non-toxic or otherwise non-deleterious. Apart from these requirements, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids, alcohols including primary and secondary alcohols, esters, carbonyl compounds including ketones and aldehydes; lactones; other cyclic organic materials including benzene derivatives, alicyclic compounds, heterocyclics such as furans, pyridines, pyrazines and the like; sulfur-containing compounds including thiols, sulfides, disulfides and the like; proteins; lipids; carbohydrates; so-called flavor potentiators such as monosodium glutamate, magnesium glutamate, calcium glutamate, guanylates and inosinates; natural flavoring materials such as cocoa, vanilla and caramel; essential oils and extracts such as anise oil, clove oil, and the like and artificial flavoring materials such as vanillin and the like.

Specific preferred flavor adjuvants are as follows:

anise oil;
ethyl-2-methyl butyrate;
vanillin;
cis-3-heptenol;
cis-3-hexenol;
trans-2-heptenol;
cis-3-heptenal;
butyl valerate;
2,3-diethyl pyrazine;
methyl cyclopentenolone;
benzaldehyde;
valverian oil;
3,4-dimethoxyphenol;
amyl acetate;
amyl cinnamate;
gamma butyryl lactone;
furfural;
trimethyl pyrazine;
phenyl acetic acid;
isovaleraldehyde;
ethyl maltol;
ethyl vanillin;
ethyl valerate;
cocoa extract;
coffee extract;
peppermint oil;
spearmint oil;
clove oil;
anethol;
cardamom oil;
wintergreen oil;
cinnamic aldehyde;
ethyl-2-methyl valerate;
gamma hexenyl lactone;
2,4-decadienal;
2,4-haptadienal; and
butylidene phthalide.

DETAILED DESCRIPTION OF DRAWINGS

The accompanying drawings illustrate products obtained by carrying out the procedures described in the examples and show slightly different peaks which represent differences in yield.

Figure 1:
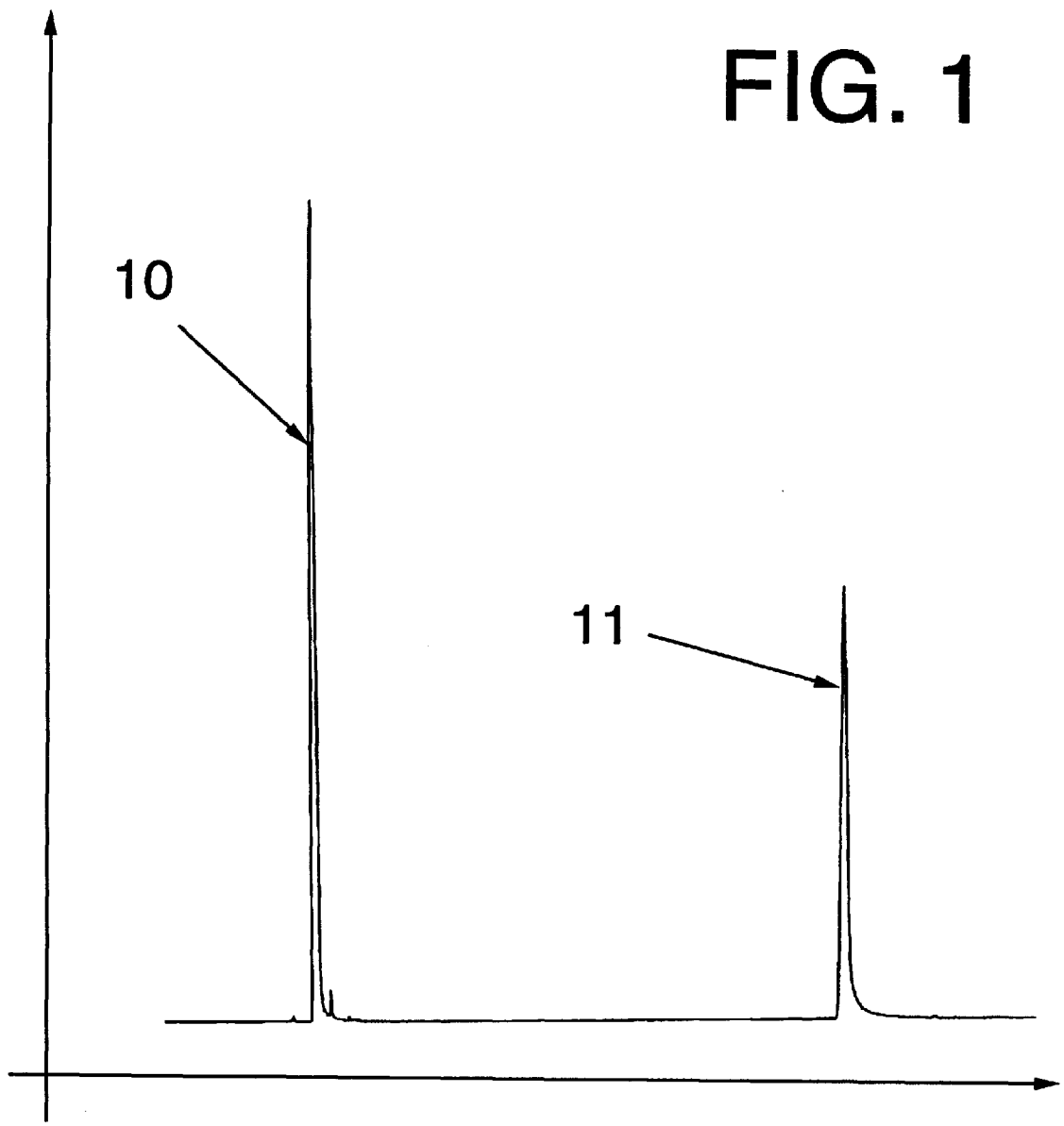
FIG. 1 is a mass spectrum of the reaction product for Example 1 containing the acetophenone compound having the structure.

FIG. 1 is a mass spectrum for the reaction product of Example 1. The peak indicated by reference numeral 10 is the peak for the compound, ethyl acetate, having the structure:

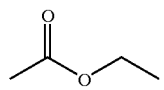

which is an impurity in the starting material.

The peak indicated by reference numeral 11 is the peak for the acetophenone compound having the structure:

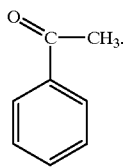

FIG. 2 is a mass spectrum for the reaction product of Example 2 and has three sections identified as A, B and C. The peak indicated by reference numeral 12 is the peak for the compound having the structure:

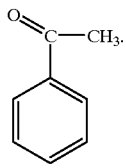

FIG. 2A is the mass spectrum for the portion of FIG. 2 indicated as 2A. The peak indicated by reference number 13 is for the compound ethyl acetate; viz:

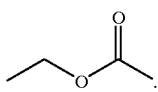

The peak indicated by the reference number 14 is for the compound propyl acetate; viz:

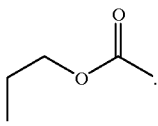

The peak indicated by the reference numbers 15 and 16 are, respectively, toluene and isobutanol.

The peak indicated by reference number 160 is for 2,3-hexaned-one. The peak indicated by reference number 161 is for ethyl benzene. The peak indicated by reference number 162 is for p-xylene. The peak indicated by reference number 163 is for m-xylene. The peak indicated by reference number 164 is for o-xylene. The peak indicated by reference number 165 is for styrene. The peak indicated by reference number 166 is for acetoin. The peak indicated by referenc number 167 is for 2,5-dimethyl pyrazine. The peak indicated by reference number 168 is for 3-hydroxy-2-pentanone.

FIG. 2B is the mass spectrum for the portion of FIG. 2 which is identified as B. The peak indicated by reference number 17 is for the compound 3-hydroxy-2-pentanone having the structure:

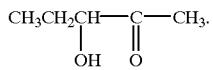

The peak indicated by the reference number 18 is for the compound 2-hydroxyl-3-pentanone having the structure:

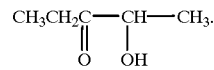

The peak indicated by the reference number 19 is for the compound 2-hydroxy-3-hexanone having the structure:

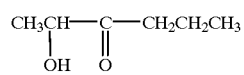

The peak indicated by the reference number 20 is for 4-heptanol having the structure:

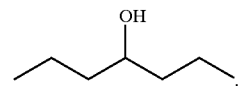

The peak indicated by the reference number 21 is for benzaldehyde having the structure:

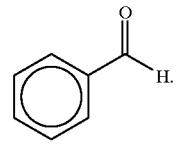

FIG. 2C is a mass spectrum for the section of FIG. 2 identified as C. The peak indicated by the reference number 22 is for acetophenone having the structure:

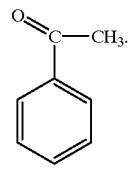

The peak indicated by the reference number 23 is for the compound α-methyl benzyl alcohol having the structure:

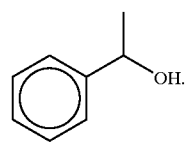

FIG. 3 is a mass spectrum for the reaction product of Example 3. The peak indicated by the reference number 24 is for acetophenone having the structure:

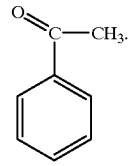

The peak indicated by the reference number 25 is for the compound α-methyl benzyl alcohol.

FIG. 4 is a mass spectrum for the reaction product of Example 4. The peak indicated by the reference number 26 is for the compound phenyl acetaldehyde having the structure:

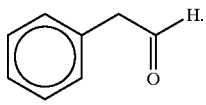

The peak indicated by the reference number 27 is for the acetophenone having the structure:

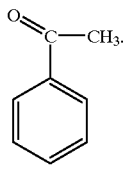

The peak indicated by the reference number 28 is for the compound methyl benzoate having the structure:

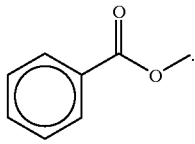

The GC-Mass Spectrum in FIG. 1 was prepared from a methyl silicon column 50 meters in height by 0.32 mm using 0.5 micron bonded fused silica, operated at an initial temperature of 75° C. up to a final temperature of 225° C. at 2° C. per minute for a total time of 30 hours.

The GC-Mass Spectrum column for FIG. 2 is a Carbonwax® 20M column 50 meters×0.32 mm using 0.3 micron nonbonded fused silica with the temperature of range 75 to 225° C. at a rate 2° C. per minute for a total time of 30 hours.

EXAMPLE 1

Acetophenone Production by *Comamonas testosteroni* ATCC 17409

A. Inoculum Preparation:
Medium:

| Ingredients | g/L |
| --- | --- |
| Bacto ® Peptone | 1.0 |
| Bacto ® Yeast Extract | 5.0 |
| $KH_2PO_4$ | 1.5 |
| $K_2HPO_4$ | 1.5 |
| $MgSO.7H_2O$ | 0.5 |
| Deionized Water | 1 L | pH = 7.0, adjusted before sterilization with 25% NaOH.

Parameters:
Temperature: 30° C.; and
Agitation: 150 rpm.

A 500 ml flask containing 100 ml of inoculum medium was sterilized at 121° C. for 20 minutes. The flask was inoculated with 1.0 ml of frozen culture of *Comamonas testosteroni* ATCC 17409, and 1.0 ml of sterile 20% sodium butyrate solution (pH 7.0) was added. The flask was incubated in a shaker (150 rpm) at 30° C. for 24 hours.

B. Acetophenone Production:

The same medium and parameters as the inoculum were used. A 500 ml flask containing 100 ml broth was sterilized for 20 min. at 121° C. A 2.5 ml aliquot of sterilized 20% sodium butyrate solution (pH 7.0) and 1 ml. of the 24 hours grown culture were added. The flask was incubated at 30° C. and 150 rpm for 24 hours. Sterile 10% sodium cinnamate (pH 7.0) was added to each flask as follows: 5 g/l at 24 hours, 4 g/l at 72 hours, and 6 g/l at 80 hours. Periodically, 2 ml. samples of broth were acidified to pH 4.0 using 50% sulfuric acid, extracted with an equal volume of ethyl acetate, and analyzed by GC. The acetophenone concentration was estimated by external standard. At the conclusion of the fermentation, the culture broth was acidified to pH 4 as above and extracted twice with ½ volume of ethyl acetate each time. The extracts were combined and solvent was removed under vacuum using a rotary evaporator. The crude product was distilled in a micro-distillation oven and the distillate analyzed by GC. The yield of 1.8 g/L having a purity of 94.3% was obtained.

EXAMPLE 2

Acetophenone Production by Arthrobacter Sp. ATCC 25581

A. Inoculum Preparation:
Medium:

| Ingredients | g/L |
| --- | --- |
| Bacto ® Peptone | 1.0 |
| Bacto ® Yeast Extract | 5.0 |
| $KH_2PO_4$ | 1.5 |
| $K_2HPO_4$ | 1.5 |
| $MgSO_4.7H_2O$ | 0.5 |
| Deionized Water | 1 L | pH = 7.0, adjusted before sterilization with 25% NaOH.

Parameters:
Temperature: 30° C.;
Agitation: 150 rpm; and
Duration: 24 hours.

A 500 ml flask containing 100 ml of inoculum medium was sterilized at 121° C. for 20 minutes. The flask was inoculated with 1.0 ml of frozen culture of Arthrobacter sp. ATCC 25581, and 1.0 ml cf sterile 50% dextrose solution was added. The flask was incubated in a shaker (150 rpm) at 30° C. for 24 hours.

B. Acetophenone Production:
Parameters:
Temperature: 30° C.;
Agitation: 100 rpm; and
Duration: 144 hours.
Medium:

| Ingredients | g/L |
| --- | --- |
| Bacto ® Yeast Extract | 5.0 |
| $(NH_4)_2SO_4$ | 1.0 |
| $KH_2PO_4$ | 1.5 |
| $K_2HPO_4$ | 1.5 |
| $MgSO_4·7H_2O$ | 0.5 |
| Deionized Water | 1 L | pH = 7.0, adjusted before sterilization with 25% NaOH.

A total of 9 Fernbach flasks, each containing 500 ml. broth, were sterilized for 30 minutes at 121° C. After cooling to room temperature, 5.0 ml. of sterile 50% dextrose solution and 5.0 ml of the 24 hour grown inoculum were added to each flask. The flasks were incubated at 30° C. at 100 rpm for 24 hours. Sterile 10% sodium cinnamate, pH 7.0, was added to each flask as follows, 5 g/l at 24 hours, 9 g/l at 48 hours, and 6 g/l at 72 hours. Samples of broth were analyzed periodically, by GC using ethyl pentanoate as an internal standard. After 44 hours of incubation, all the flasks were combined and product was extracted 3 times with ethyl acetate (approximately ½ volume each time). The combined extracts were washed 2 times with 100 ml. saturated NaHCO3 each time, followed by 2 times 100 ml saturated NaCl washes. The solvent was removed under vacuum and the crude extract was fractionally distilled to recover product. A yield of 2.7 g/L having a purity of 99.4% was obtained.

EXAMPLE 3

Acetophenone Production by Arthrobacter Sp. ATCC 25581

A. Inoculum Preparation:
Medium:

| Ingredients | g/L |
| --- | --- |
| Amberferm ® 4000 | 1.0 |
| Tastone ® 900 | 5.0 |
| $KH_2PO_4$ | 1.5 |
| $K_2HPO_4$ | 1.5 |
| $MgSO_4 \cdot 7H_2O$ | 0.5 |
| Deionized Water | 1 L | pH = 7.0, adjusted before sterilization with 25% NaOH.

Parameters:
Temperature: 30° C.;
Agitation: 150 rpm; and
Duration: 48 hours.

A 500 ml flask containing 100 ml of inoculum medium was sterilized at 121° C. for 20 minutes. The flask was inoculated with 1.0 ml of frozen culture of Arthrobacter sp. ATCC 25581, and 1.0 ml of sterile 50% dextrose solution was added. The flask was incubated in a incubator shaker (150 rpm) at 30° C. for 48 hours.

B. Acetophenone Production:
Medium:

| Ingredients | g Total |
| --- | --- |
| Tastone ® 900 | 50.0 |
| $(NH_4)_2SO_4$ | 10.0 |
| $KH_2PO_4$ | 15.0 |
| $K_2HPO_4$ | 15.0 |
| $MgSO_4 \cdot 7H_2O$ | 5.0 |
| Deionized Water | 10 L | pH = 7.0, adjusted before sterilization with 25% NaOH.

Parameters:
Temperature: 30° C.;
Aeration: 0.5 v/v/m;
Agitation: 500 rpm; and
Duration: –150 hours.

10 Liters of medium were prepared in a 14 L fermenter and were sterilized at 121° C. for 30 minutes. After sterilization, 100 g of sterile 50% dextrose solution and 100 ml of 48 hours grown inoculum were added. Periodically, after 24 hours of incubation, aliquouts of sterile 10% sodium cinnamate solution, pH 7.0 were added to maintain an approximate concentration of 5 g/L cinnamic acid.

A total of 4 batches were run. These batches were combined and the product was recovered using the same procedure as Example 3. A yield of 1.8 g/L having a purity of 99.5% was obtained.

EXAMPLE 4

Acetophenone Production by Arthrobacter Sp. ATCC 25581

A. Culture Preparation:
Medium:

| Ingredients | g/L |
| --- | --- |
| Amberferm ® 4000 | 1.0 |
| Tastone ® 900 | 5.0 |
| $KH_2PO_4$ | 1.5 |
| $K_2HPO_4$ | 1.5 |
| $MgSO_4 \cdot 7H_2O$ | 0.5 |
| Deionized Water | 1 L | pH = 7.0, adjusted before sterilization with 25% NaOH.

Parameters:
Temperature: 30° C.;
Agitation: 100 rpm; and
Duration: 48 hours.

B. Acetophenone Production:

A 500 ml of the above medium was prepared in a Fernbach flask and sterilized for 30 minutes at 121° C. The flask was inoculated with 1.8 ml. of a frozen culture of Arthrobacter sp. ATCC 25581, and 5.0 ml. of sterile 50% dextrose were added. After 48 hours of incubation, 1.0 (approx. 1.2 gm) of ethyl cinnamate was added and incubation continued.

After 48 hours of incubation following ethyl cinnamate addition, 0.09 g/L acetophenone had been formed.

EXAMPLE 5

Acetophenone Production

The procedures and media were the same as in Example 4 except for the following:

1. The inoculum was prepared in a 1 L amount and was used after 56 hours of incubation at 100 rpm;

2. A total of 14 L of broth was prepared and inoculated with 140 ml. of 56 hours grown inoculum;

3. Cinnamic acid powder was added at 25 to 49 hours of incubation, each time in 5 g/L amounts. The pH was maintained at a minimum of 7.2; and 4. After 136.4 hours of incubation, 1.85 g/L of acetophenone were formed as measured by GC.

The following examples illustrate the use of the acetophenone of this invention as component in various compositions to augment or enhance those compositions.

EXAMPLE 6

TABLE I

The following mixture is prepared:

| Ingredients | Parts by Weight |
| --- | --- |
| Orange oil | 50 |
| Bergamot oil | 20 |
| Lime oil | 100 |
| Neroli oil | 5 |
| 4-(4-Methyl-4-hydroxyamyl) delta-cyclohexene carboxaldehyde | 5 |
| 2.3.3A,4,5,7A-hexahydro--6,7A.8.8-tetramethyl-1.5,methano-1H-inden-1-ol (prepared according to the process of Example 1 of U.S. Pat. No. 3,989,760) | 100 |
| 1',2',3',4',5',6',7',8',-ocathydro-2',3',8',8'-tetramethyl-2' acetonaphthone isomer mixture (produced according to the process of Example VII U.S. Pat. No. 3,911,018) | 50 |
| γ-Methyl ionone | 20 |
| 1-Acetyl-2,5,5,-trimethylcycloheptane (produced according to U.S. Pat. No 3,869,411) | 50 |
| Acetophenone prepared according to Example 1 | 150 |

The acetophenone prepared according to Example 1 adds to this pactchouli formulation a sophisticated, intense, fruit cherry-like aroma profile with green and herbaceous topnotes.

EXAMPLE 7

Preparation of Soap Compositions

100 Grams of soap chips are produced according to Example V of U.S. Pat. No. 4,058,487, the specification for which is incorporated herein by reference as follows:

The sodium salt of an equal mixture of $C_{10}$–$C_{14}$ alkane sulfonate (95% active), 40 lbs, is dissolved in a mixture of 80 pounds of anhydrous isopropanol and 125 lbs of deionized water at 150° F. In this mixture is dissolved 10 lbs of partially hydrogenated coconut oil fatty acids and 15 lbs of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 lbs of water, 0.2 lbs of titanium hydroxide and 0.7 lbs of one of the perfume ingredients set forth in Table II below. The chips are then plodded into logs, cut to size and finally stamped into bars having a pH of approximately 6.9.

Each of the perfumed soaps produced by means of the foregoing procedure manifests an excellent aroma as set forth in Table II, infra:

TABLE II

| Ingredient | Fragrance Profile |
| --- | --- |
| Acetophenone produced according to Example 1. | A cherry aroma with sweet, creamy, nut-like topnotes and heavy, fruity undertones. |
| The perfume composition of Example 6 | A patchouli aroma with cherry-like undertones. |

EXAMPLE 8

Preparation of a Detergent Composition

A total of 100 grams of a detergent powder prepared according to U.S. Pat. No. 4,058,472 (the specification for which is incorporated by reference herein) and containing 5% $C_{14}$–$C_{18}$ alkyl catechol as a surface active component. The mixture being 60 parts by weight of mono-$C_{14}$–$C_{18}$ alkyl catechol, 35% sodium tetrapyrophosphate, 30% sodium silicate, 20% of sodium carbonate, 3% of sodium carboxymethyl cellulose and 7% of starch is mixed with 0.15 grams individually with each of the aroma ingredients set forth in Table II of Example 7 until a substantially homogeneous composition is obtained. Each of the compositions has an excellent aroma as set forth in Table II of Example 7.

EXAMPLE 9

Preparation of a Cosmetic Powder Composition

A cosmetic powder is prepared by mixing in a ball mill, 100 grams of talcum powder with 0.25 grams of each of the perfume materials of Table II of Example 7. Each of the powders has an excellent aroma as set forth in Table II of Example 7.

EXAMPLE 10

Perfumed Liquid Detergent

Concentrated liquid detergents with aromas as set forth in Table II of Example 7 are prepared by adding 0.10%, 0.15% and 0.20% of each of the ingredients set forth in Table II of Example 7. They are prepared by adding and homogeneously mixing the appropriate quantity of perfume substance of Table II of Example 7 in the liquid detergent. The detergents individually possess aromas as set forth in Table II of Example 7, the intensity increasing with greater concentration of perfume substances set forth in Table II of Example 7.

EXAMPLE 11

Preparation of a Cologne Handkerchief Perfume

Each of the ingredients of Table II of Example 7 is incorporated individually into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%, 85%, 90% and 95% aqueous ethanol). Distinct and definite aromas as set forth in Table II of Example 7 are imparted to the colognes and to the handkerchief perfumes at the several concentrations set forth above.

EXAMPLE 12

Preparation of Soap Compositions

100 Grams of soap chips (IVORY® produced by the Proctor & Gamble Company of Cincinnati, Ohio) are admixed with one gram of each of the substances set forth in Table II of Example 7, supra, until homogenous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table II of Example 7.

EXAMPLE 13

Preparation of Solid Detergent Compositions

Detergents are prepared from the following ingredients according to Example I of Canadian Patent No. 1,007,948, the specification for which is incorporated by reference herein:

| Ingredients | Parts by Weight |
|---|---|
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a "phosphate-free" detergent. A total of 100 grams of said detergent is admixed with 0.10, 0.15, 0.20 and 0.25 grams of each of the substances set forth in Table II of Example 7, supra. Each of the detergent samples has an excellent aroma as indicated in Table II of Example 7.

EXAMPLE 14

Preparation of Drier-Added Fabric Softener Article

Utilizing the procedure of Example I at column 15 of U.S. Pat. No. 3,632,396 the specification for which is incorporated by reference herein, a non-woven cloth substrate useful as a drier-added fabric softening article of manufacture is prepared wherein the substrate, substrate coating and outer coating and the perfume material are as follows:

1. a water "dissolvable" paper ("Dissolve Paper") as the substrate;
2. ADOGEN® 448 (melting point about 140° F.) as the first substrate coating; and
3. an outer coating having the following formulation (melting point about 150° F.)
   57% $C_{20}$–$C_{22}$ HAPS;
   22% isopropyl alcohol;
   20% antistatic agent; and
   1% of one of the perfumery substances set forth in Table II of Example 7, supra.

Fabric softening compositions containing the substances as set forth in Table II of Example 7, supra, essentially consist of a substrate having a weight of about 3 grams per 100 square inches; a substrate coating weighing about 1.85 grams per 100 square inches of substrate; and an outer coating weighing about 1.5 grams per 100 square inches of substrate are prepared thereby providing a total aromatized substrate and outer coating weight ratio of about 1:1 by weight of the substrate.

The aromas as set forth in Table II of Example 7, supra, are imparted in a pleasant manner to the head space in a drier on operation thereof using the said drier-added fabric softening non-woven fabric by adding to the drying cycle.

As stated above in the case of fabric softener articles, the entire U.S. Pat. No. 3,632,396 is incorporated by reference herein. Thus, all of the articles of U.S. Pat. No. 3,632,396 acting as fabric softening articles in said U.S. patent may be perfumed in their outer coating with from 0.25% up to 5% by weight of each of the perfuming substances of Table II of Example 7, supra.

EXAMPLE 15

Hair Preparation

A "soft-feel, good-hold" hair spray is produced containing the following ingredients:

| Ingredients | Parts by Weight |
|---|---|
| Polyvinylpyrollidone/vinyl acetate "E-735 Copolymer" manufactured by the GAF Corporation of New York, NY | 4.00 |
| Anhydrous ethanol | 70.90 |
| Dioctyl sebecate | 0.05 |
| Benzyl alcohol | 0.05 |
| "Propellant A46" manufactured by the GAF Corporation of New York, NY | 24.95 |
| Fragrance ingredient as set forth in Table II of Example 7, supra. | 0.05 |

The PVP/VA copolymers are first dissolved in alcohol and all other ingredients are added until uniform. The propellant is then pressurized and used as an aerosol. The resulting hair sprays each have pleasant aromas as set forth in Table II of Example 7.

EXAMPLE 16

Scouring Cleanser Composition

A scouring cleanser composition is prepared in accordance with Example I at columns 11 and 12 of U.S. Pat. No. 4,193,888 issued on Mar. 18, 1980, the specification for which is incorporated by reference herein. To this composition, the substances set forth in Table II of Example 7, supra, are added at the level of 0.25% as set forth in the table in said Example I of U.S. Pat. No. 4,193,888 yielding an aroma on using said cleanser in ordinary circumstances which is quite pleasant and described in Table II of Example 7, supra.

EXAMPLE 17

A fabric softening article prepared substantially as set forth in Example VII of Canadian Patent No. 1,069,260, the specification for which is incorporated by reference herein, is prepared containing 0.21% by weight of a perfuming substance as set forth in Table II of Example 7, supra, and yielding on use in a drier, a faint aroma as set forth in Table II of Example 7, supra.

EXAMPLE 18

Pudding

At the rate of 0.8 ppm (i) the acetophenone produced according to Example 1 is added to a ROYAL® butterscotch pudding. Pleasant aesthetically pleasing cherry nuances were added to the butterscotch pudding with the panel of 30 members to prefer the butterscotch pudding with the acetophenone added thereto to a butterscotch pudding without the acetophenone added thereto.

EXAMPLE 19

Flavor Formulations

The following natural rich orange formulations are prepared:

| Ingredient | Parts by Weight |
| --- | --- |
| Compound defined according to the structure: | 26.0 |

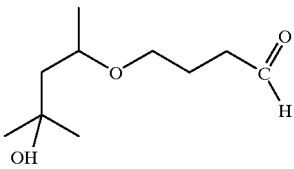

prepared according to Example VI of U.S. Pat. No. 4,532,364.

| | |
| --- | --- |
| The acetophenone produced according to Example 1 | 12.00 |
| Natural lemon oil terpeneless | 10.0 |
| Acetaldehyde | 0.6 |
| α-Terpineol | 2.1 |
| Citral | 1.8 |
| Carvone | 0.24 |
| Terpinolene | 1.2 |
| α-Terpinene | 0.25 |
| Diphenyl | 0.25 |
| α-Fenchyl alcohol | 0.25 |
| Limonene | 0.35 |
| Linalool | 0.25 |
| Gereanyl acetate | 0.25 |
| Nootkatone | 0.25 |
| Neryl acetate | 0.25 |

A second flavor formulation is prepared which is identical to the above formulation, except without the acetophenone of Example 1.

The flavor formulation with the acetophenone of Example 1 has a definite natural rich orange aroma with buttery nuances due to the addition of buttery principals to this citrus flavor.

The acetophenone of Example 1 added thereto is used in the following examples.

EXAMPLE 20

A. Powder Flavor Compositions

20 Grams of the flavor compositions of Examples 19 containing the acetophenone of Example 1 is emulsified in a solution containing 300 grams gum acacia and 700 grams water. The emulsion is spray-dried with a Bowen Lab Model Drier utilizing 260 c.f.m. of air with an inlet temperature of 500° F., an outlet temperature of 200° F., and a wheel speed of 50,000 rpm.

B. Sustained Release Flavor

| Ingredients | Parts by Weight |
| --- | --- |
| Liquid citrus flavor compositions of Example 19 | 20.0 |
| Propylene glycol | 9.0 |
| CAB-O-SIL ® (Brand of Silica produced by the Cabot Corporation of 125 High Street Boston, MA 0210): Physical Properties: | 5.00 |
| Surface area: 200 m₂/gm | |
| Nominal particle size: 0.012 microns | |
| Density: 2.3 lbs/cu. ft.) | |

The CAB-O-SIL® is dispersed in the liquid citrus flavor composition of Example 19 with vigorous stirring, thereby resulting in each case in a viscous liquid. 71 Parts by weight of the powder flavor compositions of Part "A", supra, is then separately blended into the said viscous liquid, with stirring, at 25° C. for a period of 30 minutes resulting in dry, free flowing sustained release flavor powder.

EXAMPLE 21

10 Parts by weight of 50 Bloom pigskin gelatin is added to 90 parts by weight of water at a temperature of 150° F. The mixture is agitated until the gelatin is completely dissolved and the solution is cooled to 120° F. Separately, 20 parts by weight of the liquid flavor composition of Examples 19 is added to the solution which is then homogenized to form an emulsion having particle size typically in the range of 5–40 microns. This material is kept at 120° F. under which conditions the gelatin will not jell.

Coacervation is induced by adding, slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixtures into 1,000 parts by weight (each) of 7% aqueous solutions of sodium sulphate at 65° C. The resulting jelled coacervates may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE 22

Chewing Gum

100 Parts by weight of chicle are mixed with 4 parts by weight of the flavor prepared in accordance with Example 19. 300 Parts of sucrose and 100 parts of corn syrup are added. Mixing is effected in a ribbon blender with jacketed side walls of the type manufactured by the Baker Perkins Company.

The resultant chewing gum blend is then each manufactured into strips 1 inch in width and 0.1 inches in thickness. The strips are cut into lengths of 3 inches each. On chewing, the chewing gum has a pleasant, long-lasting rich citrus flavor.

EXAMPLE 23

Chewing Gum

100 Parts by weight of chicle are mixed with 18 parts by weight of the flavor prepared in accordance with Example 19. 300 Parts of sucrose and 100 parts of corn syrup are then added. Mixing is effected in a ribbon blender with jacketed side walls of the type manufactured by the Baker Perkins Company.

The resultant chewing gum blend is then manufactured into strips 1 inch in width and 0.1 inches in thickness. The strips are cut into lengths of 3 inches each. On chewing each of, the chewing gums has a pleasant, long-lasting rich citrus flavor.

EXAMPLE 24

Toothpaste Formulation

The following separate groups of ingredients are prepared:

| Ingredients | Parts by Weight |
|---|---|
| Group "A" | |
| Glycerine | 30.200 |
| Distilled water | 15.325 |
| Sodium benzoate | 0.100 |
| Saccarin sodium | 0.125 |
| Stannous fluoride | 0.400 |
| Group "B" | |
| Calcium carbonate | 12.500 |
| Dicalcium phosphate (dihydrate) | 37.200 |
| Group "C" | |
| Sodium N-lauroyl sarcosinate (foaming agent) | 2.000 |
| Group "D" | |
| Flavor material of Example 19 | 1.200 |

1. The ingredients in Group "A" are stirred and heated in a steam jacketed kettle to 160° F.;
2. Stirring is continued for an additional three to five minutes to form a homogeneous gel;
3. The powders of Group "B" are added to the gel, while mixing, until a homogeneous paste is formed;
4. With stirring, one of the flavors "D" is added and lastly the sodium n-lauroyl sarcosinate;
5. The resultant slurry is then blended for one hour.

The completed paste is then transferred to a three roller mill and then homogenized, and finally tubed.

The resulting toothpastes when used in normal toothbrushing procedures yield pleasant rich citrus flavors, of constant strong intensity throughout said procedure (1–1.5 minutes).

EXAMPLE 25

Chewable Vitamin Tablets

The flavor material produced according to the process of Example 19 is added to a chewable vitamin tablet formulation a rate of 10 gm/Kg which chewable vitamin tablet formulation is prepared as follows:

In a Hobart Mixer the following materials are blended to homogeneity:

| Ingredients | Gms/1,000 Tablets |
|---|---|
| Vitamin C (ascorbic acid as ascorbic acid-sodium ascorbate mixture 1:1 | 70.0 |
| Vitamin B$_1$ (thiamine mononitrate) as ROCOAT ® thiamine mononitrate 33⅓ (Hoffman La Roche) | 4.0 |
| Vitamin B$_2$ (riboflavin) as ROCOAT ® riboflavin 33⅓% | 5.0 |
| Vitamin B$_6$ (pyridoxine hydrochloride) as ROCOAT ® pyridoxine hydrochloride 33⅓% | 4.0 |
| Niacinamide as ROCOAT ® niacinamide 33⅓% | 33.0 |
| Calcium pantothenate | 11.5 |
| Vitamin B$_{12}$ (cyanocobalamin) (Merck) 0.1% in gelatin | 3.5 |
| Vitamin E (dl-alpha tocopheryl acetate) as dry Vitamin E acetate 33⅓% Roche | 6.6 |
| d-Biotin | 0.004 |
| The flavor of Example 19 | (as indicated above) |
| Certified lake color | 5.0 |
| Sweetner - sodium saccharin | 1.0 |
| Magnesium stearate lubricant | 10.0 |
| Mannitol | (q.s. to make) 500.0 |

Preliminary tablets are prepared by slugging with flat-faced punches and grinding the slugs to 14 mesh. 13.6 g dry Vitamin A acetate and 0.6 g Vitamin D are then added as beadlets. The entire blend is then compressed using concave punches at 0.5 g each.

Chewing of the resultant tablets yields pleasant, long-lasting, consistently strong rich citrus flavors for a period of 12 minutes.

EXAMPLE 26

To 100 parts by weight of GOYA® mango nectar (produced by the Goya Corporation of New York, N.Y.) is added 10 ppm of the acetophenone produced according to Example 1. The acetophenone adds to the mango nectar a very natural nuance which although present in natural mango (prior to adding the acetophenone of Example 1) is lost in the canning process when the mango nectar is prepared and canned in the usual manner.

We claim:

1. A process for the high-yield production of acetophenone represented by the structural formula:

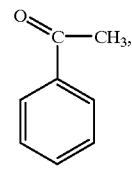

comprising:
 (i) preparing an aqueous nutrient medium as a first aqueous liquid phase, containing a source of carbon, a nitrogen source, a buffer and yeast extract at a neutral pH of about 7;
 (ii) inoculating said first aqueous liquid phase with a bacteria species being a member selected from the group consisting of Arthrobacter ATCC 25581 and Comamonas testosteroni ATCC 17409, and incubating for a sufficient period of time with agitation to produce a grown culture of said bacteria species;
 (iii) preparing an acetophenone production medium a mixture containing a carbon source, a nitrogen source, a buffer and yeast extract at a neutral pH of about 7;
 (iv) mixing said grown culture and said acetophenone production medium together with agitation to form a reaction medium;
 (v) feeding a source of cinnamic acid to said reaction medium at a rate sufficient to maintain a concentration in the range of 5–10 grams per liter of said cinnamic acid source and at a rate sufficient to enable said bacteria species to maintain oxidative growth; and
 (vi) aerating with an oxygen-containing gas at a rate enabling interaction with said carbon source to avoid production of unwanted alcohol in a sufficient amount to maintain oxidative conditions throughout the reaction to thereby achieve an oxidation reaction in the presence of said bacteria species capable of producing said natural acetophenone compound in a high yield.

2. A reaction product produced by the process according to claim 1 and having a mass spectrum consisting essentially of ethyl acetate (10) and acetophenone (11).

3. A reaction product produced by the process according to claim 1 and having a mass spectrum consisting essentially of acetophenone (12) and (22), ethyl acetate (13), propyl acetate (14), toluene (15), isobutanol (16), 3-hydroxy-2-pentanone (17) and (168), 2-hydroxy-3pentanone (18), 2-hydroxy-3-hexanone (19), 4-heptanol (20), benzaldehyde (21), (α-methyl benzyl alcohol (23), 2,3-hexanedione (160), ethyl benzene (161), p-xylene (162), m-zylene (163), o-xylene (164), styrene (165), and 2,5-dimethyl pyrazine (167).

4. A reaction product produced by the process according to claim 1 and having a mass spectrum consisting essentially of acetophenone (24) and α-methyl benzyl alcohol (25).

5. A reaction by the process according to claim 1 and having a mass spectrum consisting essentially of phenyl acetaldehyde (26), an acetophenone (27), and methyl benzoate (28).

6. A foodstuff composition consisting essentially of a foodstuff base and intimately admixed therein a flavor augmenting, enhancing or imparting quantity and concentration of the reaction product defined according to claim 2.

7. A foodstuff composition consisting essentially of a foodstuff base and intimately admixed therein a flavor augmenting, enhancing or imparting quantity and concentration of the reaction product defined according to claim 3.

8. A foodstuff composition consisting essentially of a foodstuff base and intimately admixed therein a flavor augmenting, enhancing or imparting quantity and concentration of the reaction product defined according to claim 4.

9. A foodstuff composition consisting essentially of a foodstuff base and intimately admixed therein a flavor augmenting, enhancing or imparting quantity and concentration of the reaction product defined according to claim 5.

10. A process for augmenting, enhancing or imparting the aroma and taste in or to a consumable material selected from the group consisting of foodstuffs and chewing gums comprising the step of intimately admixing an aroma and taste augmenting, enhancing or imparting amount and concentration of the reaction product defined according to claim 2.

11. A process for augmenting, enhancing or imparting the aroma and taste in or to a consumable material selected from the group consisting of foodstuffs and chewing gums comprising the step of intimately admixing an aroma and taste augmenting, enhancing or imparting amount and concentration of the reaction product defined according to claim 3.

12. A process for augmenting, enhancing or imparting the aroma and taste in or to a consumable material selected from the group consisting of foodstuffs and chewing gums comprising the step of intimately admixing an aroma and taste augmenting, enhancing or imparting amount and concentration of the reaction product defined according to claim 4.

13. A process for augmenting, enhancing or imparting the aroma and taste in or to a consumable material selected from the group consisting of foodstuffs and chewing gums comprising the step of intimately admixing an aroma and taste augmenting, enhancing or imparting amount and concentration of the reaction product defined according to claim 5.

* * * * *